(12) United States Patent
Gattiker et al.

(10) Patent No.: US 11,226,313 B2
(45) Date of Patent: Jan. 18, 2022

(54) APPARATUS AND DEVICE FOR TESTING A COMPONENT BY MEANS OF ULTRASOUND

(71) Applicant: PROCEQ SA, Schwerzenbach (CH)

(72) Inventors: Felix Gattiker, Zurich (CH); Marco Osterwalder, Wetzikon (CH); Marcel Poser, Oberuzwil (CH)

(73) Assignee: PROCEQ SA, Schwerzenbach (CH)

( * ) Notice: Subject to any disclaimer, the term of this patent is extended or adjusted under 35 U.S.C. 154(b) by 292 days.

(21) Appl. No.: 16/340,894

(22) PCT Filed: Oct. 11, 2016

(86) PCT No.: PCT/CH2016/000132
§ 371 (c)(1),
(2) Date: Apr. 10, 2019

(87) PCT Pub. No.: WO2018/068156
PCT Pub. Date: Apr. 19, 2018

(65) Prior Publication Data
US 2019/0285591 A1  Sep. 19, 2019

(51) Int. Cl.
*G01N 29/22* (2006.01)
*G01N 33/38* (2006.01)

(52) U.S. Cl.
CPC ......... *G01N 29/226* (2013.01); *G01N 33/383* (2013.01)

(58) Field of Classification Search
CPC .... G01N 29/226; G01N 33/383; G01N 29/36; G01N 2291/0232; G01N 2291/105; G01N 29/22
See application file for complete search history.

(56) References Cited

U.S. PATENT DOCUMENTS

| 7,587,943 B2 | 9/2009 | Wiggenhauser |
| 2009/0027736 A1 | 1/2009 | Brignac |
| 2009/0088645 A1 | 4/2009 | Shin |
| 2009/0303064 A1 | 12/2009 | Labreck |
| 2009/0326380 A1 | 12/2009 | Shin |
| 2011/0013486 A1 | 1/2011 | Bond-Thorley |

(Continued)

FOREIGN PATENT DOCUMENTS

| EP | 2 044 887 | 4/2009 |
| EP | 2 901 936 | 8/2015 |

(Continued)

OTHER PUBLICATIONS

PCT Documents in PCT/CH2016/00132.

(Continued)

*Primary Examiner* — Herbert K Roberts
*Assistant Examiner* — John M Royston
(74) *Attorney, Agent, or Firm* — Greenblum & Bernstein, P.L.C.

(57) ABSTRACT

An apparatus for testing a component by ultrasound comprises a plurality of identical devices. Each device has several channels of ultrasonic transducers as well as a master controller. The individual devices are daisy-chained and controlled by one of their master controllers. Mechanical connectors can be used to mechanically couple adjacent devices. Further, a number of differently shaped handles is provided, all of which can be coupled to a common handle interface.

21 Claims, 5 Drawing Sheets

(56) References Cited

U.S. PATENT DOCUMENTS

2013/0018525 A1    1/2013   Jang
2015/0182197 A1    7/2015   Willems
2015/0190114 A1    7/2015   Ninomiya
2017/0299460 A1*   10/2017   Duerr .................... G01N 29/24

FOREIGN PATENT DOCUMENTS

| JP | 2009-506328 | 2/2009 |
| JP | 2012-225746 | 11/2012 |
| JP | 3182773 | 3/2013 |
| RU | 2010107242 | 9/2011 |
| RU | 2010/145060 | 5/2012 |
| WO | 2007/025109 | 3/2007 |

OTHER PUBLICATIONS

Russian Search Report (with English translation) dated Jan. 10, 2020.

Japanese Office Action (with English translation) dated Aug. 11, 2020 and issued in JPO 2019-519393.

* cited by examiner

A (2:1)

APPARATUS AND DEVICE FOR TESTING A COMPONENT BY MEANS OF ULTRASOUND

TECHNICAL FIELD

The invention relates to an apparatus and a device for testing a component, such as a body of concrete or another building component, by means of ultrasound.

BACKGROUND ART

The destruction-free testing of components by means of ultrasound provides an important tool in various fields of technology. It can e.g. be used to locate reinforcements, voids, cracks or inhomogeneities in building materials, such as concrete.

A device of this type is shown in U.S. Pat. No. 7,587,943. It comprises a plurality of ultrasonic transducers arranged in a housing. Driver electronics are provided for individually sending and/or receiving signals through the transducers.

To operate the device, the user holds the same against the component to be tested, and then the transducers are operated to perform a scanning operation.

DISCLOSURE OF THE INVENTION

In a first aspect of the invention, the problem to be solved is to provide an apparatus and device of this type that is easy to handle by a user.

This problem is solved by a device for testing a component by means of ultrasound comprising the following items:

A housing: The housing forms the mechanical frame of the device.

A plurality of ultrasonic transducers: The transducers are arranged on a probing side of the housing. They are bidirectional transducers and can be operated to receive as well as to emit ultrasonic waves. The measurement can be carried out by holding the probing side of the housing with the transducers against the component to be tested.

Driver electronics: The driver electronics are arranged in the housing and are adapted and structured for operating the transducers.

A mechanical handle interface arranged on the housing: The mechanical handle interface is shaped for mounting at least one handle to the housing.

A set of differently shaped handles: Each handle is structured to be mounted on the mechanical handle interface.

By providing the device with a set of differently shaped handles, it can be adapted to the user's needs more easily.

The "set of differently shaped handles" is to be understood as comprising a plurality of handles, with at least two of these handles shaped differently from each other.

Advantageously, the mechanical handle interface of the device is structured and adapted to alternatively receive one as well as two of the handles at a time. In other words, depending on current requirements (e.g. depending on how many hands he wants to use for holding the device), the user can mount one handle, but he can also mount two handles.

The mechanical handle interface can comprise a plurality of mechanical adapters located on a "first mounting side" of the housing. This first mounting side, which can, in particular, be a flat or curved surface of the device, is arranged transversally, in particular perpendicularly, to the probing side of the housing. In this context, "perpendicular" is advantageously indicative of an angle of 90°+/−10°. The first mounting side extends between a first and a second end face of the housing.

Advantageously, the set of handles comprises at least one "first handle". This first handle has a foot section adapted and structured to be connected to at least one of the adapters, in particular by being shaped to mate with said at least one adapter. It also has a grip section to be gripped by a user. The grip section is positioned such that, when the first handle is mounted to the housing, the grip section extends away from said housing at a center between the first and said second end face of the housing. In this context, "at a center" is advantageously understood such that the distances of the grip section from the first and the second end faces differ by no more than 10%.

Such a first handle allows to hold the device centrally, typically with a single hand.

The device can also comprise at least one "second handle". The second handle has a foot section adapted and structured to be connected to at least one of the adapters, in particular by being shaped to mate with said at least one adapter. It also has a grip section to be gripped by the user. The second handle is shaped such that, when said second handle is mounted to the housing, the grip section projects over the first or the second end face of the housing.

In this case, the set of handles advantageously comprises at least two of the second handles, and the mechanical handle interface is adapted and structured to receive two of the second handles at the same time, with the grip sections of the mounted handles being arranged on opposite sides of said housing. This set-up is especially convenient when the user wants to hold the device with both hands.

In another advantageous embodiment, the device further comprises an electrical handle interface arranged on its housing. This electrical handle interface is structured to provide an electrical connection to at least one of the handles mounted to the mechanical handle interface. Further, at least part of the handles comprises a user-operatable element, such as a button, a slider or a switch, by means of which the device can be controlled through the electrical handle interface. In this context, the term "control" is to be understood as an operation controlling at least one aspect of the device. For example, the user-operatable element can be used to trigger a measurement, to adjust an amplification, to change a mode of measurement or to change the operating mode of a display on the device, etc.

Advantageously, the electrical handle interface comprises a set of contacts members on the side of the device as well as on the side of the handle that automatically come into contact with each other when the handle is mounted to the device.

The invention also relates to an apparatus for testing a component by means of ultrasound. The apparatus comprises several devices of the type above as well as at least one mechanical connector. In other words, the apparatus is a set of several of the devices and further comprises said mechanical connector. The mechanical connector is structured and adapted to mechanically connect two of the devices to each other by being attached to the mechanical handle interfaces of these two devices.

In a second aspect of the invention, the problem to be solved is to provide an apparatus for testing a component by means of ultrasound that provides freedom for configuring a measurement according to a user's needs.

This problem is solved by an apparatus comprising a plurality of identical devices, wherein each device comprises A housing: The housing forms the mechanical frame of the device.

A plurality of ultrasonic transducers: The transducers are arranged on a probing side of the housing. They are bidirectional transducers and can be operated to receive as well as to emit ultrasonic waves. The measurement can be carried out by holding the probing side of the housing with the transducers against the component to be tested.

Driver electronics: The driver electronics are arranged in the housing and are adapted and structured for operating the transducers.

A peer device interface: This interface is adapted and structured for establishing communication with at least one other device of the devices of the apparatus.

A master controller: The master controller is adapted and structured to control said at least one other device through the peer device interface.

In other words, the apparatus comprises a plurality of identical devices. Each of these devices comprises ultrasonic transducers as well as said peer device interface and said master controller. The master controller is able to control at least one, in particular all, of the other devices of the apparatus through the peer device interface. Hence, every device in the apparatus can act as a master device that is able to control one or more other devices of the apparatus. This improves the flexibility when assembling several devices into a complex measurement architecture.

In the present context, two devices are considered to be "identical" if they have the same functional, electric and mechanical design as well as the same firmware. They may differ, however, in non-functional aspects, such as in their color or their serial number.

Advantageously, each device comprises several channels, with each channel including at least one of the transducers. In other words, each transducer is attributed to a channel. Each channel has a send mode for sending ultrasonic signals as well as a receive mode for receiving ultrasonic signals. The master controller of each device is adapted and structured to locally and individually control the mode of the channels on the same device as well as to remotely and individually control the mode of the channels on said at least one other device.

Hence, in this embodiment, one master controller can individually control the channels on the device it belongs to as well as the mode of operation of the channels of another device via the peer device interface. This renders the architecture more versatile in that a single master controller can control a larger number of channels. In particular, the master controller is adapted to configure some of the channels of another device to be in send mode and some others in receive mode.

The peer device interface advantageously comprises a data link adapted and structured to transmit information describing a signal to be generated in said send mode and/or describing a signal received in said receive mode, thus enabling the (currently active) master controller to control the sent out signals and/or to collect the received signals of the individual channels of its own and other devices.

In addition to the data link, the peer device interface can comprise a real-time trigger link adapted and structured to synchronize the devices in time. In this case, the data link can form a non-real-time connection between the devices. In this context, the term "non-real-time connection" refers advantageously to a connection whose signals are not synchronized with the ultrasonic pulses.

The apparatus can further comprise a host unit adapted and structured to controlling the apparatus. In other words, the host unit provides a means for the user to control the operation of the apparatus. This host unit is separate from the devices, and it advantageously has a housing separate from the housings of the devices. In this case, the devices can remain identical and simple while there is still a dedicated piece of equipment that forms a central control of the apparatus.

In this case, each device further comprises a host data interface adapted and structured to connect the master controller of the device to the host unit. The host unit is adapted and structured to connect to the master controller of a first one of the devices and to control all devices through the master controller of this first device. In other words, it is sufficient to connect the host unit to a single one of the devices for controlling all of them.

In order to finely tune a measurement through the host unit, the host data interface can be adapted and structured to transmit information describing the signal to be generated in the send mode and/or describing the signal received in the receive mode individually for each of the channels of the apparatus. Hence, the host unit can control each channel individually and/or receive the measured signal from teach individual channel.

Also, the host data interface can be adapted and structured to individually control the mode of all channels of said apparatus. This allows to fully configure the send and receive patterns of the whole apparatus through the host unit.

The apparatus and device according to the present invention can be used to probe any type of sample, in particular samples of concrete.

BRIEF DESCRIPTION OF THE DRAWINGS

The invention will be better understood and objects other than those set forth above will become apparent when consideration is given to the following detailed description thereof. This description makes reference to the annexed drawings, wherein.

MODES FOR CARRYING OUT THE INVENTION

Figure 1:
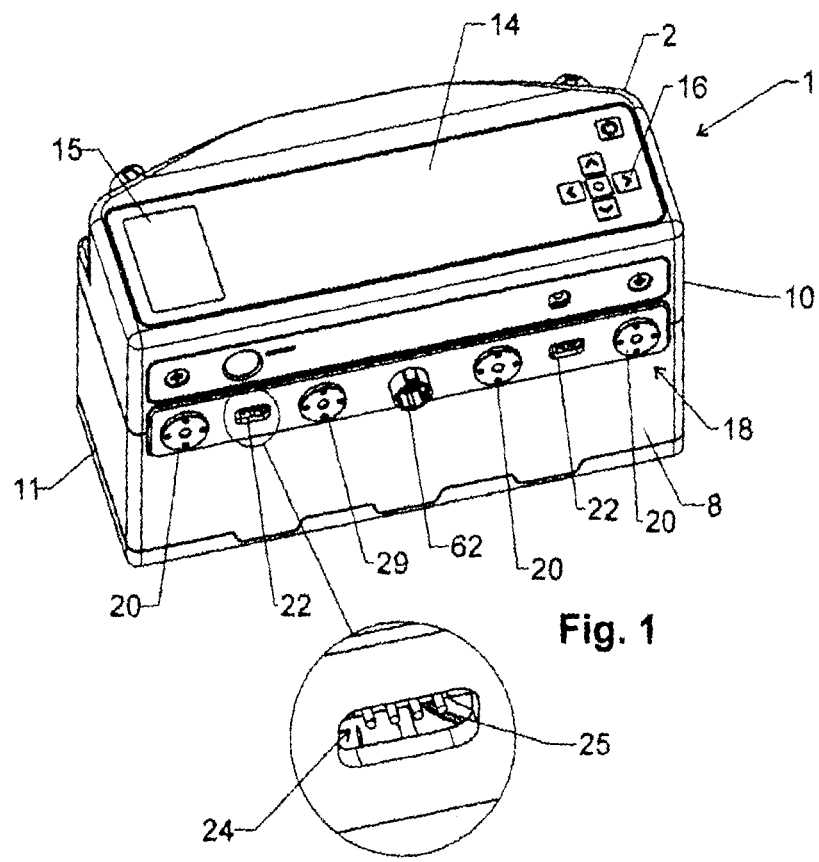
FIG. 1 shows a device for testing a component by means of ultrasound from its first mounting side.

Housing Design:

The device 1 shown in FIG. 1 can be used for the non-destructive testing of a component by means of ultrasound.

It comprises a housing 2 of e.g. substantially cuboid design.

Figure 2:
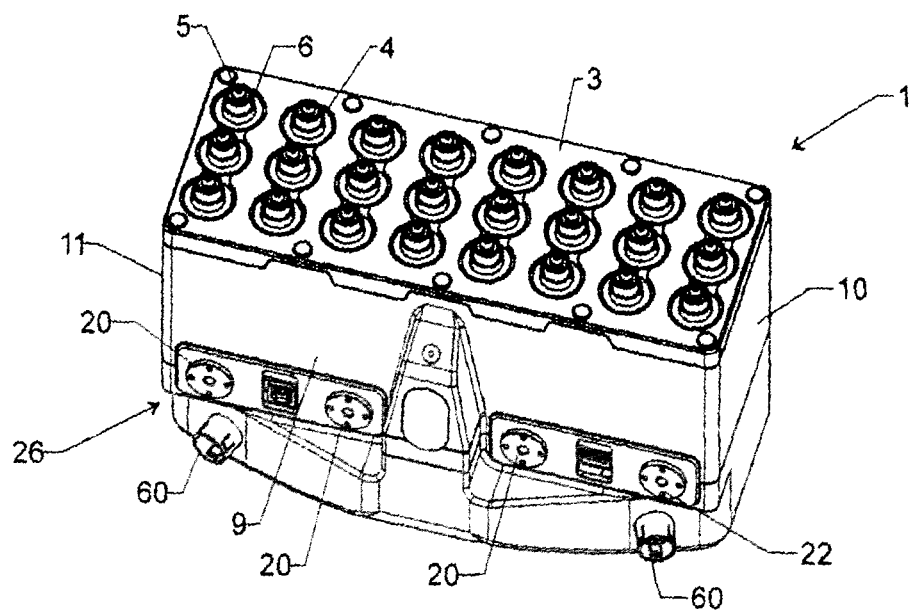
FIG. 2 shows the device of FIG. 1 from its second mounting side.

Housing 2 has a probing side 3, which is best seen in FIG. 2. Probing side 3 is advantageously flat.

A plurality of bidirectional ultrasonic transducers 4 is arranged on probing side 3 of housing 2. Each transducer 4 advantageously comprises a piezoelectric actuator equipped with a tip 5 and elastically mounted in a holder 6, e.g. of the type described in WO 2016/029326.

The transducers 4 are advantageously arranged in a rectangular matrix of rows and columns. In the present embodiment, this matrix has three such rows and eight columns. The transducers 4 in a single column can e.g. be part of a single channel of the device, as it will be described in more detail below.

Housing 2 further comprises a first and a second mounting side 8, 9. Both of them are transversal, in particular perpendicular, to probing side 3. They extend, just as probing side 3, between a first end face 10 and a second end face 11 of housing 2.

Finally, housing 2 comprises a user interface surface 14, which is advantageously located opposite to probing surface 3. As shown in FIG. 1, user interface surface 14 can hold user interface elements, such as a display 15 and user-operatable controls 16.

As best seen in FIG. 1, a mechanical handle interface, generally denoted by 18, is arranged on first mounting side 8. Handle interface 18 comprises a plurality of mechanical adapters 20, advantageously at least four of them. In the embodiment of FIG. 1, the mechanical adapters 20 are arranged in a row.

In addition, an electrical handle interface 22 is also arranged on mounting side 8. Advantageously, electrical handle interface 22 comprises at least two connectors 24 with contact members 25. In the embodiment of FIG. 1, the connectors 24 are arranged in a row with the mechanical adapters 20.

In particular, there can be four mechanical adapters 20 in a row and two electrical connectors 24. In this case, when numbering the mechanical adapters along the row as a first to fourth mechanical adapter, the first connector 24 is located between the first and second mechanical adapter, while the second connector 24 is located between the third and fourth mechanical adapter. In this case, the electrical adapters can be contacted not only by a symmetric handle, as shown e.g. in FIG. 3, but also be a lateral handle connecting to the outmost two mechanical adapters only, such as shown in FIGS. 4 and 5 and described in more detail below.

As shown in FIG. 2, the device further can comprise an auxiliary mechanical interface 26, again formed by e.g. of a plurality mechanical adapters 20, arranged on second mounting side 9.

Figure 3:
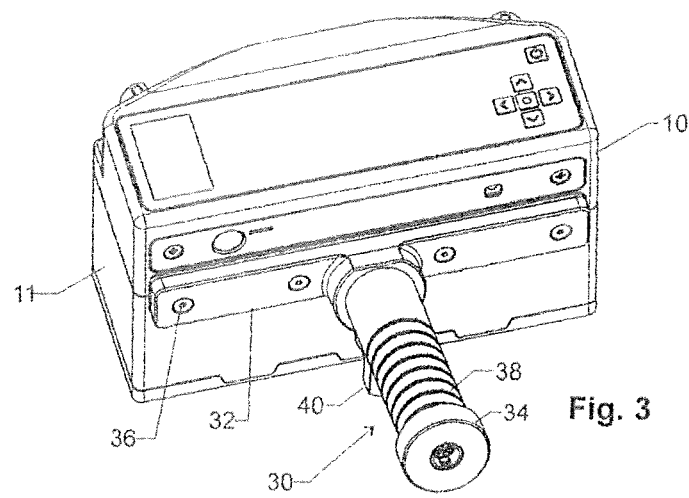
FIG. 3 shows the device of FIG. 1 with a first handle attached thereto.
Figure 4:
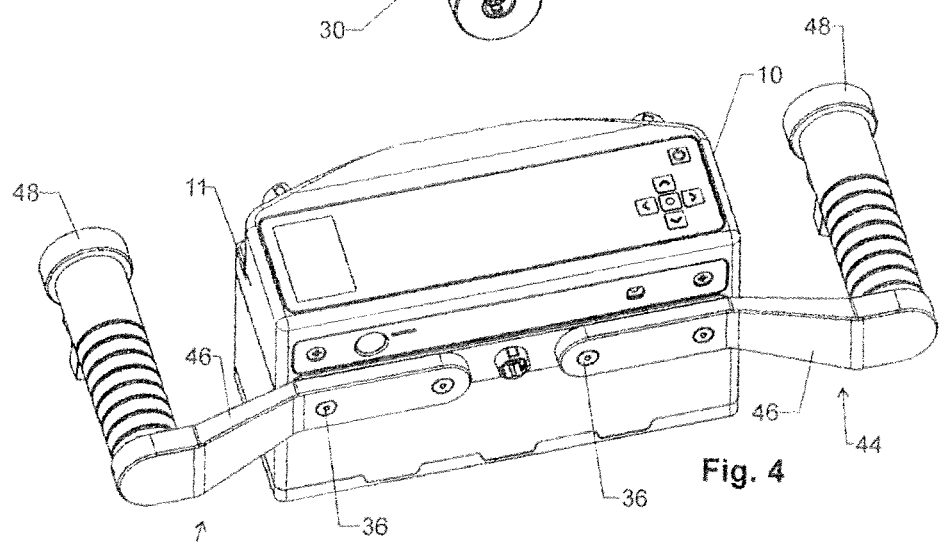
FIG. 4 shows the device of FIG. 1 with two second handles attached thereto.
Figure 5:
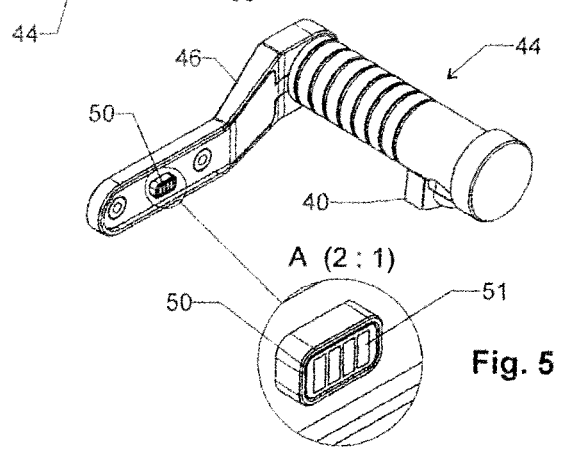
FIG. 5 shows a single second handle of the device.

Handle Design:

The device is designed to be connected to a plurality of different handles, as shown in FIGS. 3 and 4. The purpose of these handles is to provide a handhold for the user for holding the device while performing a measurement.

FIG. 3 shows a first handle 30, which is intended to allow the user to hold the device with a single hand.

First handle 30 is of symmetrical design and comprises a foot section 32 as well as a grip section 34. Foot section 32 is adapted and structured to connect to at least one, in particular to at least two, of the adapters 20, in the present embodiment to all of the adapters 20. For example, screws 36 can be located in foot section 32, with each screw being screwed into one of the adapters 20.

Grip section 34 is advantageously mounted to the center of foot section 32 in order to have a symmetric distribution of forces.

Advantageously, grip section 34 comprises a grip surface 38 designed to provide a firm grip to the user.

When first handle 30 is mounted to housing 2, grip section 34 is located at the center between the first and said second end faces 10, 11 of device 1 and extends away from housing 2. Advantageously, grip section 34 extends perpendicularly to a line connecting the first and second end faces 10, 11.

First handle 30 further comprises a user-operatable element 40 for controlling at least one operation of device 1 through electrical handle interface 22.

While first handle 30 is designed to hold device 1 with a single hand, FIGS. 4 and 5 show two second handles 44, which are optimized to hold the device with two hands.

Each second handle 44 has a foot section 46 and a grip section 48. Foot section 46 is adapted and structured to connect to at least one, in particular to at least two, of the adapters 20, in the present embodiment to half of the adapters 20 of mechanical handle interface 18 of device 1. Again, screws 36 can be located in foot section 46 and be screwed into the mechanical adapters 20.

As can best be seen in FIGS. 4 and 5, grip section 48 extends transversally, advantageously perpendicularly, to foot section 46, such that each second handle is substantially L-shaped.

When a second handle 44 is mounted to housing 2, grip section 48 extends beyond the first or the second end face 10, 11 of housing 2.

As shown in FIG. 4, mechanical handle interface 18 is structured to receive two of the second handles 44 at the same time, with their grip sections 48 being arranged on opposite sides of housing 2, i.e. housing 2 is located between the grip sections 48 of the two second handles 44.

Each second handle 44 is advantageously also provided with a user-operatable element 40 for controlling at least one operation of device 1.

In particular, user-operatable element 40 of the first and/or second handle 30, 44 can control at least one of the following functions of the device 1:

It can be used to trigger a measurement.

It can be used to store a measurement.

It can be used to select a gain of the channels that are in receive mode.

It can be used to select another parameter of the measurement, such as a filtering mode or a pulse shape.

FIG. 5 shows how a connector 50, mating with connector 24 of device 1, can be arranged at foot section 46 of second handle 44. It comprises a number of contact members 51 that come into contact with the contact members 25 of connector 24 when the handle is mounted to the device. At least one similar connector can also be located at foot section 32 of first handle 30.

It is up to the user to decide if the device is to be operated with the first handle 30 or the second handles 44, depending on the intended mode of use. The handles can be swapped easily.

Further types of handles can be included with the apparatus. For example, a handle may also have a grip section located above (i.e. in a space extending perpendicularly outwards from) user interface surface 14.

Device Interconnection:

As will be described in more detail below, several of the devices 1 can be assembled into an apparatus in order to increase the number of measurement channels and/or the distance between them.

In this case, each device 1 can be held by a user individually. However, in an advantageous embodiment, the apparatus comprises at least one mechanical connector structured and adapted to mechanically connect at least two of the devices 1 to each other. This is illustrated in FIG. 6.

Figure 6:
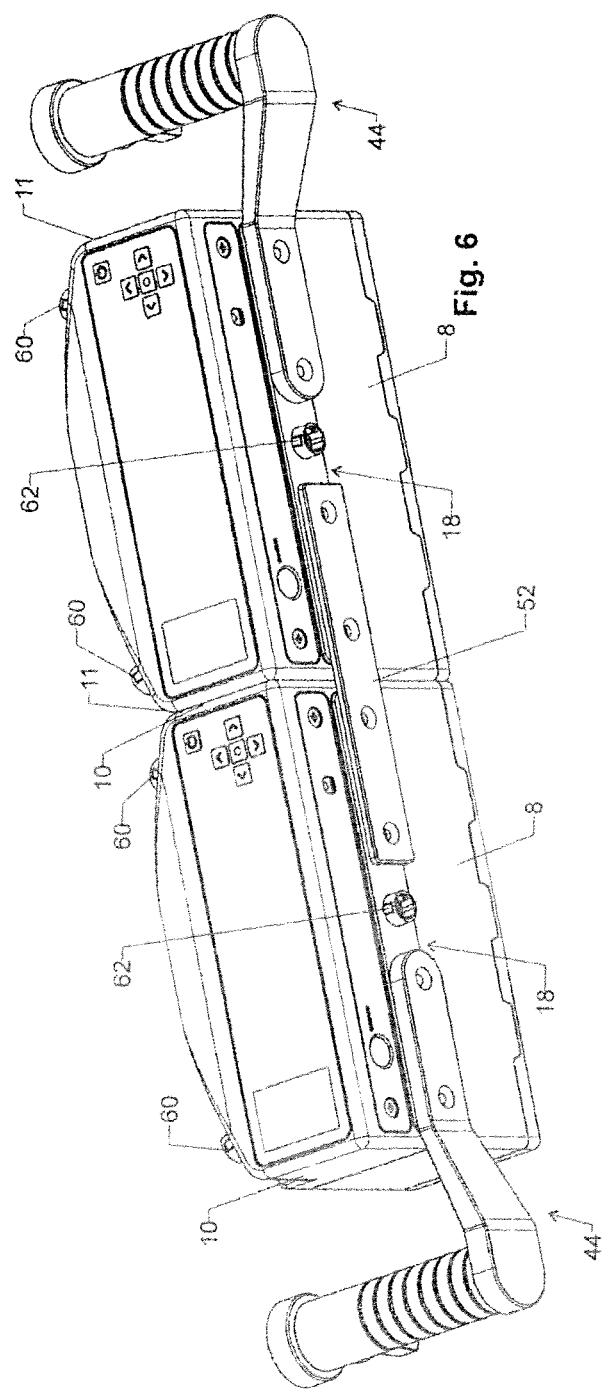
FIG. 6 shows two mechanically connected devices of FIG. 1 with two of the second handles attached to them.

In the embodiment of FIG. 6, mechanical connector 52 is designed to be attached to the mechanical handle interfaces 18 of the two devices 1.

Advantageously, the devices 1 and the mechanical connector 52 are structured such that the devices 1 can be mounted with second end face 11 of a first one of the devices being adjacent to first end face 10 of a second one of the devices. To do so, mechanical connector 52 is mounted to a first part of the mechanical adapters 20 at first mounting side 8 of the housings 1 of the first and the second device.

In the embodiment of FIG. 6, mechanical connector 52 is mounted to half of the mechanical adapters of mechanical handle interface 18 of each device 1.

In this configuration, and as shown in FIG. 6, two of the second handles 44 can be mounted to the second part of the mechanical adapters 20 of mechanical handle interface 18 of each device 1.

In order to reinforce the mechanical connection between the two devices, a second mechanical connector, advantageously of the same design as mechanical connector 52, can also be mounted to the mechanical connectors 20 on second mounting side 9 of each device.

Apparatus Circuitry:

When operating several devices 1 in a single apparatus, means for synchronizing and for central control must be available. For this purpose, each device 1 is advantageously equipped with a peer device interface so as well as with a host interface. Both of these interfaces can be wire-bound or wireless.

In the embodiment of FIGS. 1-6, the peer device interfaces are equipped with plug-connectors 60 for forming a daisy chain of all the devices 1 of the apparatus.

Similarly, in the embodiment of FIG. 1-6, the host interface of each device is equipped with a plug-connector 62.

Figure 7:
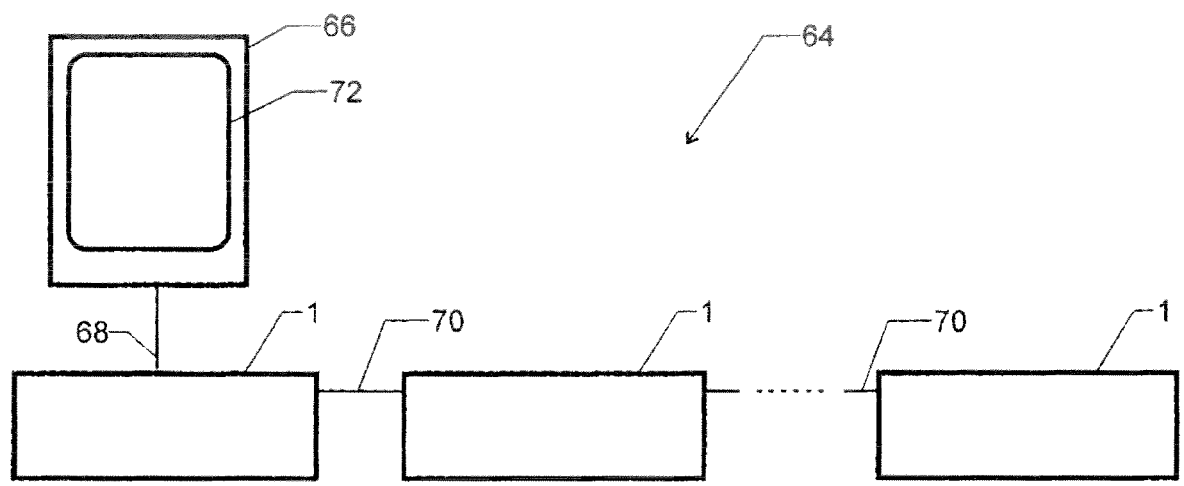
FIG. 7 is a block diagram of an apparatus comprising a plurality of the devices.

A possible architecture of a complete apparatus 64 with several devices 1 is shown in FIG. 7.

The apparatus 64 comprises a host unit 66 connected to one of the devices 1 by means of a host connection 68, while the devices 1 are daisy-chained by means of device connections 70.

Host unit 66 can e.g. be a tablet computer. It typically comprises a display 72 for displaying measurement data and a graphical user interface, as well as user controls, e.g. being implemented by using a touch-sensitive device as display 72.

Host unit 66 forms the central control unit of apparatus 64. It is able to receive configuration data from the user, e.g. a specification of which of the channels of the device are to emit a signal and which of them are to receive signals. It is also able to send the user inputs as commands to the devices 1, operate them accordingly, and receive measurement data in return. In can process these measurement data and display the results in a user-readable manner on display 72. It can also comprise means for storing or further processing the measurement data.

Figure 8:
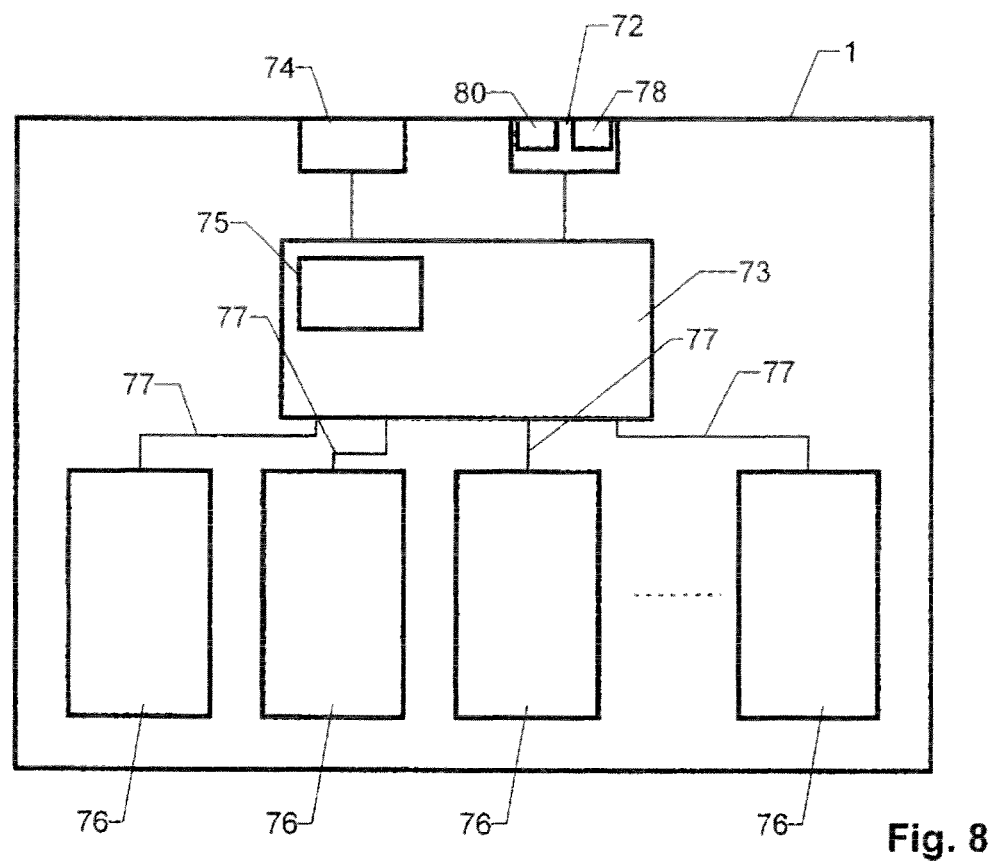
FIG. 8 is a block diagram of a single device.

FIG. 8 shows a block diagram of a single device 1. As mentioned, each device comprises a peer device interface 72 for establishing communication with at least one other device of the apparatus, e.g. in a daisy chain configuration as described above, via the device connections 70.

It also comprises a master controller 73 that is able to control the other devices of the apparatus.

Further, each device comprises a host data interface 74 to connect master controller 73 to host unit 66 via host connector 68.

Finally, each device 1 comprises a plurality of channels 76, each of which includes at least one of the transducers 4. In the embodiment shown here, each channel 76 comprises three of the transducers 4.

The functions of these components are now described in further detail.

Master controller 73 is used to control the function of its own device as well as the function of the other devices of the apparatus. In other words, if the apparatus 64 comprises N>1 devices 1, it also comprises N master controllers 73, each of which is theoretically able to control all other devices. However, only the master controller 73 whose device 1 is connected to host unit 66 via host data interface 74 will assume this role (thereby acting as the "active master controller"), while the other master controllers 73 will only act as local controllers for their respective devices.

Alternatively, or in addition thereto, the active master controller can be the one controller at the end of the daisy chain of the devices 1.

Master controller 73 advantageously comprises a CPU as well as FPGA circuitry, interconnected e.g. by means of a fast serial bus. The FPGA is used to generate all digital signals for which precise timing is required, e.g. for generating the clock signals for the analog/digital converters of the channels. The CPU, on the other hand, controls the measuring procedure and the high-level aspects of the communication with the other devices, i.e. it is responsible for those tasks where precise timing is not required.

Each of the channels 76 has a send mode for sending ultrasonic signals as well as a receive mode for receiving ultrasonic signals. Master controller 73 is able to locally control the mode of the channels 76 on its own device. In addition, the active master controller 73, e.g. the one that is directly connected to host unit 66, is able to remotely control the mode of the channels 76 on the other devices 1 by sending appropriate signals through peer device interface 72.

Peer device interface 72 comprises a data link 78 for transmitting information describing a signal to be generated in the send mode of the individual channels as well as for describing a signal received in the receive mode by the individual channels.

Data link 78 is advantageously configured to transmit one or more of the following items of information:

- Information as to which channels are in "receive mode", i.e. configured to receive signals, or in "send mode", i.e. configured to send signals. This information is sent from the active master controller 73 to the individual channels 76.
- Information describing the signal to be generated by those channels that are in send mode. This information may include signal shape, signal amplitude, signal phase (or signal delay), and it is sent from the active master controller 73 to the individual channels 76.
- Information describing the signal received by the channels. This information can e.g. contain a series of sampled signal amplitudes during a certain time interval, and it is sent from the individual channels 76 to the active master controller 73.
- Information about receiver settings, such as amplifier gain, sampling rate and/or filter parameters.

Peer device interface 72 also comprises a trigger link 80 adapted and structured to synchronize all the devices 1 in time. In other words, even though each device 1 typically has its own clock generator, a trigger signal can be sent from the active master controller to all devices in order to establish a common time reference on all of them, thereby allowing to send signals that are mutually synchronized and to receive signal data with a common time base. Trigger link 80 can e.g. be a simple signal line that switches its level when a measurement is to start, once that all necessary set-up information has been distributed though data link 78.

As mentioned above, data link 78 advantageously forms a non-real-time connection, thereby allowing the data to be transferred asynchronously between the devices 1. This is particularly useful when a large amount of measurement data is to be transferred from the individual devices 1 to the active master controller.

In order to be able to sample, in real-time, the measurement data describing the signals received from the channels 76 while transmitting the same later, in non-real-time, to the active master controller, each master controller advantageously comprises a memory 75 adapted to buffer the measurement data from the channels 76.

In order to increase data throughput, and as shown in FIG. 8, each channel 76 has its own data connection 77 to its local master controller 73, thereby increasing the speed of data transfer between the channels 76 and master controller 73 as compared to a communication via an common data bus where the channels 76 have to be addressed and queried consecutively.

Figure 9:
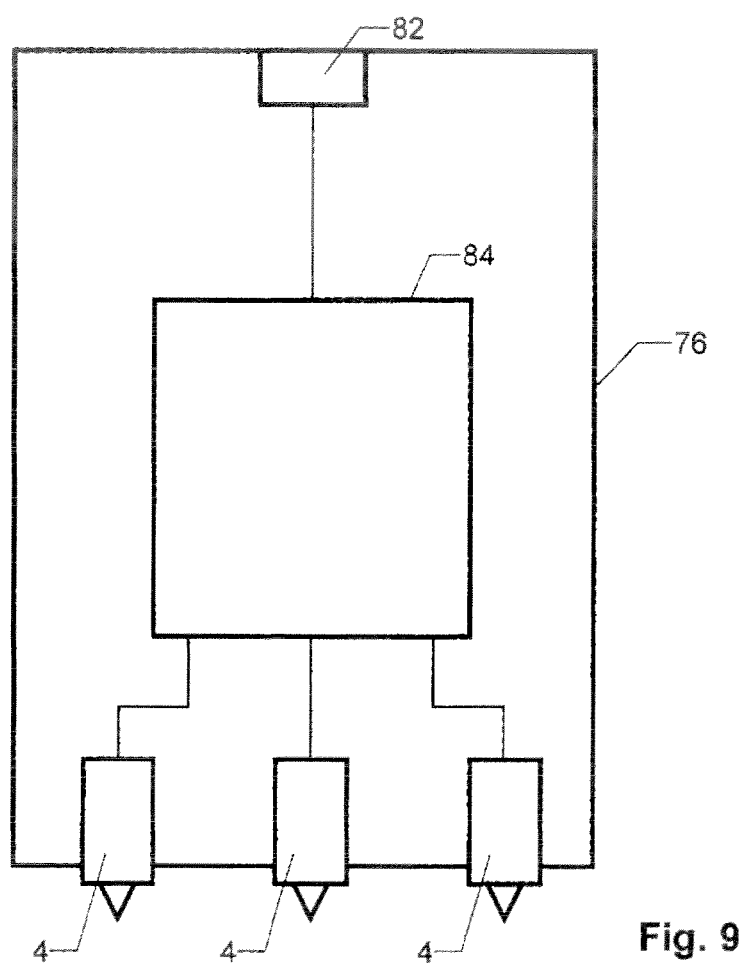
FIG. 9 is a block diagram of a channel of a device.

FIG. 9 finally shows a block diagram of a single channel 76. It comprises a channel interface 82 for interfacing with the local master controller 73 of the same device. Driver electronics 84 are provided for generating electrical signals in order to activate the transducers 4 of the channel as well as for receiving and amplifying the signals received by the transducers 4. Driver Electronics 84 can contain analog-digital as well as digital-analogue converters, in which case the transfer of data over channel interface 82 to the local master controller 73 can be digital.

Notes:

Handle interface 18 can also be used to attach components other than handles. In particular, handle interface 18 can be used to mount device 1 to a robotic manipulator that automatically moves the device to desired locations of measurement on a sample to be examined. In this case, the mechanical adaptors 20 are used to establish a mechanical connection to the manipulator, while the electrical handle interface 22 can establish an electronic connection allowing to automatically trigger a measurement.

The adapter 20 can e.g. comprise projections extending over mounting side 8, and the foot sections of the handles can include recesses for receiving these projections, or vice versa, thereby forming a mating connection between the foot section and the adaptors.

The apparatus is highly scalable. The number of devices 1 in an apparatus can be large if a complex measurement is to be carried out.

The devices 1 of an apparatus can be mechanically coupled to each other, such as shown in FIG. 6, or they can be separate from each other, only connected to each other electronically over the peer device interfaces 72.

The devices 1 can be used to measure reflected as well as transmitted signals.

The modes "send mode" and "receive mode" are not exclusive. In particular, a channel may be configured to be in send mode, but at the same time in receive mode, e.g. in order to receive an echo after sending out a pulse.

The apparatus is particularly suited for creating a phased array where the channels generate mutually phase-shifted signals. Alternatively, or in addition thereto, the apparatus can be operated in SAFT mode where one channel is in send mode and the others are in receive mode, with the master controller changing the channel that is in send mode between consecutive measurements. Individual measurements can be triggered by means of the active master controller and/or by host unit 66. Measurements can be running continuously in order to obtain a real-time image on display 72 of host unit 66. In this case, individual measurements can be stored, e.g. by operating user-operatable element 40 on one of the handles.

Each device 1 can have its own power supply, such as a rechargeable battery.

While there are shown and described presently preferred embodiments of the invention, it is to be distinctly understood that the invention is not limited thereto but may be otherwise variously embodied and practiced within the scope of the following claims.

The invention claimed is:

1. A device for testing a component by ultrasound comprising:
   a housing,
   a plurality of bidirectional ultrasonic transducers arranged at least partially in said housing on a probing side of said housing,
   driver electronics arranged in said housing for operating said transducers,
   a mechanical handle interface arranged on said housing for mounting a handle, and
   a set of differently shaped handles, wherein each handle is structured to be mounted on said mechanical handle interface to position the probing side for testing the component.

2. The device of claim 1, wherein said mechanical handle interface is structured to receive one as well as two of said handles at a time.

3. The device of claim 1, wherein said mechanical handle interface comprises a plurality of mechanical adapters located on a first mounting side of said housing, wherein said first mounting side is transversal, in particular perpendicular, to said probing side and extends between a first and a second end face of the housing.

4. The device of claim 3, comprising at least one first handle having a foot section adapted and structured to connect to at least one of said adapters as well as a grip section to be gripped by a user, wherein, when said first handle is mounted to said housing, said grip section is located at a center between said first and said second end face and extends away from said housing.

5. The device of claim 4, wherein said foot section is adapted and structured to connect to at least two of said adapters when being mounted to said housing and wherein said grip section is mounted to a center of said foot section.

6. The device of claim 3, comprising at least one second handle having a foot section adapted and structured to connect to at least one of said adapters as well as a grip section to be gripped by the user, wherein, when said second handle is mounted to said housing, said grip section projects over the first or the second end face of the housing.

7. The device of claim 6, comprising at least two of said second handles, wherein said mechanical handle interface is adapted and structured to receive two of said second handles at the same time, with the grip sections of said second handles being arranged on opposite sides of said housing.

8. The device of claim 6, wherein said grip section of said second handle extends transversally, in particular perpendicularly, to the foot section of said second handle.

9. The device of claim 1, further comprising an electrical handle interface arranged on said housing for providing an electrical connection to at least one of said handles mounted to said mechanical handle interface, and wherein at least part of said handles comprises a user-operatable element for controlling the device through said electrical handle interface.

10. An apparatus for testing a component by ultrasound comprising several devices of claim 1, and further comprising at least one mechanical connector, wherein said mechanical connector is structured and adapted to mechanically connect at least two of said devices to each other by being attached to said mechanical handle interfaces of the two devices.

11. The apparatus of claim 10, wherein said devices and said mechanical connector are structured such that said devices can be mounted with the second end face of a first one of said devices being adjacent to the first end face of a second one of said devices by mounting said mechanical connector to a first part of said mechanical adapters at the first mounting side of the housing of the first and the second device.

12. The apparatus of claim 11, wherein, when said first and second devices are mounted with the end faces adjacent to each other and said mechanical connector is mounted to said first part of said mechanical adapters, two of said second handles can be mounted to a second part of said mechanical adapters.

13. An apparatus claim 10, for testing a component by ultrasound comprising a plurality of identical devices, wherein each device comprises:
- a housing,
- a plurality of identical, bidirectional ultrasonic transducers arranged in or on said housing,
- driver electronics arranged in said housing for operating said transducers,
- a peer device interface for establishing communication with at least one other device of said devices, and
- a master controller adapted and structured to control said at least one other device through said peer device interface.

14. The apparatus of claim 13, wherein each device comprises several channels, each channel including at least one of said transducers, in particular several of said transducers, and having a send mode for sending ultrasonic signals as well as a receive mode for receiving ultrasonic signals, wherein the master controller of each device is adapted and structured to locally and individually control the mode of the channels on the same device as well as to remotely and individually control the mode of the channels on said at least one other device.

15. The apparatus of claim 14, wherein said peer device interface comprises a data link adapted and structured to transmit information describing a signal to be generated in said send mode and/or describing a signal received in said receive mode.

16. The apparatus of claim 15, wherein said peer device interface comprises a trigger link adapted and structured to synchronize said devices in real-time, wherein said data link forms a non-real-time connection.

17. The apparatus of claim 14, wherein said master controller comprises a memory for buffering measurement data describing signal received by said channels.

18. The apparatus of claim 13,
- wherein said apparatus further comprises a host unit for controlling said apparatus, wherein said host unit is separate from said devices,
- wherein each device further comprises a host data interface adapted and structured to connect the master controller of said device to said host unit, and
- wherein said host unit is adapted and structured to connect to the master controller of a first one of said devices to control all of said devices through the master controller of the first device.

19. The apparatus of claim 14, wherein said host data interface is adapted and structured to transmit information describing a signal to be generated in said send mode and/or describing a signal received in said receive mode individually for each of the channels of the apparatus.

20. The apparatus of claim 14, wherein said host data interface is adapted and structured to individually control the mode of all channels of said apparatus.

21. A method for testing a component by ultrasound with the device of claim 1, comprising:
- orienting the plurality of bidirectional ultrasonic transducers toward the component,
- wherein the component tested is concrete.

* * * * *